United States Patent [19]

Lokkesmoe et al.

[11] Patent Number: 5,122,538

[45] Date of Patent: Jun. 16, 1992

[54] PEROXY ACID GENERATOR

[75] Inventors: Keith D. Lokkesmoe, Burnsville; Thomas R. Oakes, Stillwater, both of Minn.

[73] Assignee: Ecolab Inc., St. Paul, Minn.

[21] Appl. No.: 556,892

[22] Filed: Jul. 23, 1990

[51] Int. Cl.$^5$ .............. C07C 179/133; C07C 179/00; A61K 31/19
[52] U.S. Cl. ..................................... 514/557; 562/6; 562/562; 514/572
[58] Field of Search .................. 514/557, 572; 562/2, 562/6

[56] References Cited

U.S. PATENT DOCUMENTS

| | | | |
|---|---|---|---|
| 2,910,540 | 10/1959 | Hawkinson et al. | 260/502 |
| 3,528,115 | 9/1970 | Lawes | 8/111 |
| 4,051,058 | 9/1977 | Bowing et al. | 252/186 |
| 4,051,059 | 9/1977 | Bowing et al. | 252/186 |
| 4,225,451 | 9/1980 | McCrudden et al. | 562/2 |
| 4,278,615 | 7/1981 | Stober et al. | 260/502 |
| 4,297,298 | 10/1981 | Crommelynck et al. | 260/502 R |
| 4,370,251 | 1/1983 | Liao et al. | 562/6 |
| 4,529,534 | 7/1985 | Richardson | 252/100 |
| 4,647,678 | 3/1987 | Eckwert et al. | 549/528 |

FOREIGN PATENT DOCUMENTS

| | | |
|---|---|---|
| 24219 | 2/1981 | European Pat. Off. |
| 136280 | 4/1985 | European Pat. Off. |
| 195619 | 3/1986 | European Pat. Off. |
| 231632A2 | 12/1986 | European Pat. Off. |
| 269435A2 | 11/1987 | European Pat. Off. |
| 3638552A1 | 5/1988 | Fed. Rep. of Germany |
| 1128870 | 1/1957 | France |
| 776758 | 6/1957 | United Kingdom |

OTHER PUBLICATIONS

"Proxitane 1507 in Industrial Laundries", a technical brochure available from Interox America, Oct. 1988.

"Novel Application of Peracetic Acid in Industrial Disinfection":, J. A. L. Fraser, *Specialty Chemicals*, Jun. 1987, pp. 178-186.

"Dequest ® 2010 Phosphonate, Dequest 2000 and 2006 Phosphonates and Dequest 2060 and 2066 Organophosphorus Compounds", Technical Bulletin No. 9024, 9023 and Publication O. WT-8601, respectively.

"Preparation of Peracetic Acid by Using Various Catalyst Systems", Agnihotri et al., *Colourage*, vol. 18, No. 26, p. 30 (1973).

"Influence of Nature of Cation Exchange Resin on Reaction of Acetic Acid with Hydrogen Peroxide", Chalabiev et al., *Kinetics and Catalysis*, vol. 24, No. 1, pp. 78-82 (1983).

*Primary Examiner*—Frederick E. Waddell
*Assistant Examiner*—Diane Gardner
*Attorney, Agent, or Firm*—Merchant, Gould, Smith, Edell, Welter & Schmidt

[57] ABSTRACT

We have found a new and useful process to generate peroxy acid sanitizing and bleaching compositions at the point-of-use, the process comprising introducing hydrogen peroxide and a carboxylic acid into a reactor at about 0.1 to 10 moles of hydrogen peroxide per mole of acid, and contacting the hydrogen peroxide and carboxylic acid in the presence of a sulfonic acid resin and in the substantial abssence of active metal ions which forms an aqueous peroxy acid composition at a concentration from about up to 20 wt %. Using this process, warewashing, laundry sanitizing and bleach, and hard surface sanitizing compositions can be produced.

30 Claims, 1 Drawing Sheet

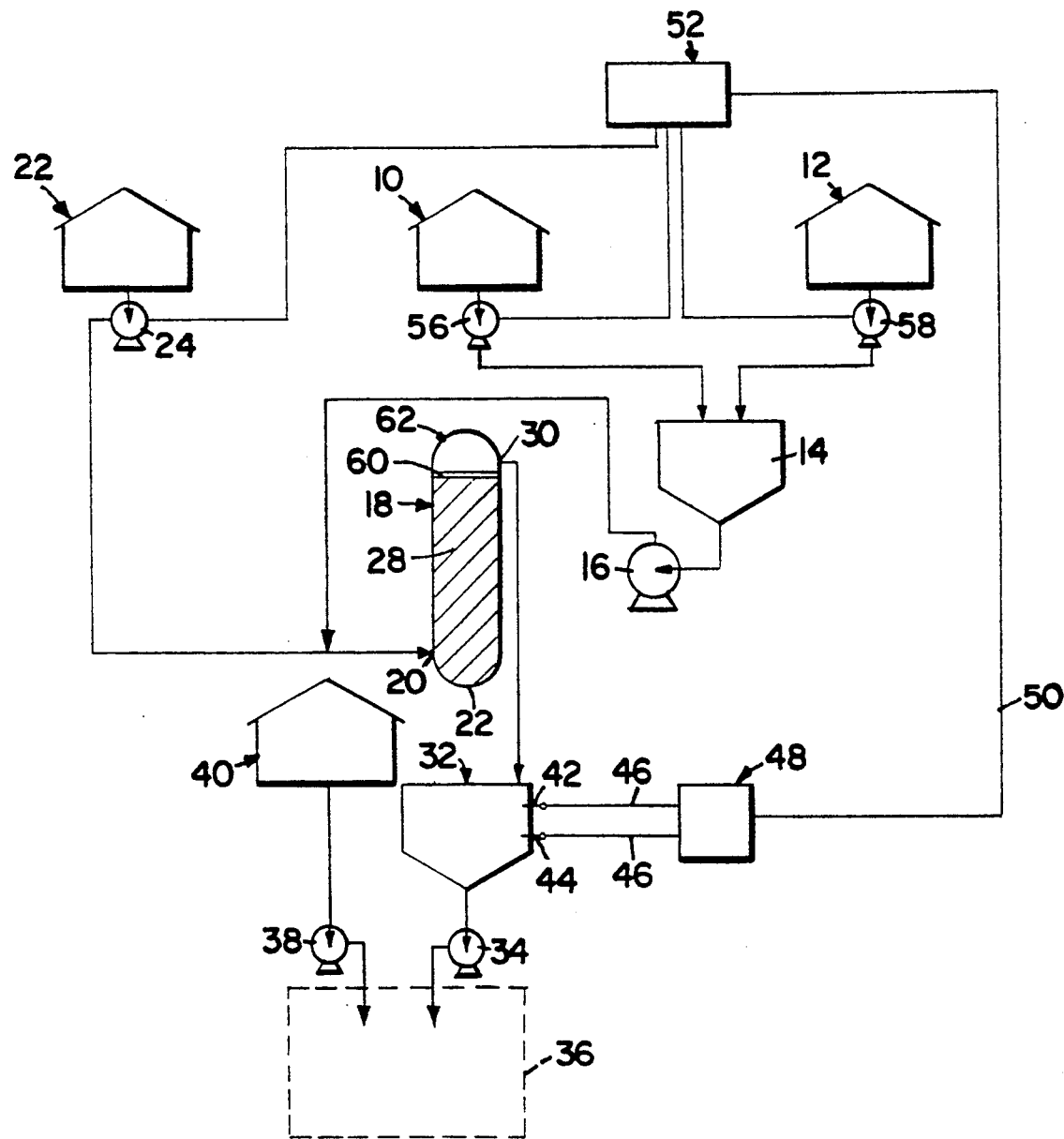

PEROXY ACID GENERATOR

FIELD OF THE INVENTION

This invention relates to the manufacture and use of peroxy acid compounds. More particularly, it relates to the generation of peroxy acid sanitizing compositions at the point of use.

BACKGROUND OF THE INVENTION

Peroxy acid compounds have been used for cleaning or sanitizing processes. The peroxy acids have been produced in large quantities and then shipped to the use site in either dilute or concentrated form. Neither of these options is particularly desirable. Shipping dilute solutions of peroxy acids i.e., about 5% peroxy acid in water, increases shipping costs due to the dilute nature of the product, while shipping more concentrated peroxy acids is a potentially hazardous process as peroxy acids can be explosive.

The peroxy acid compositions have been stabilized with known additives for long term storage. Bowing et al, U.S. Pat. No. 4,051,058 teach peroxy containing concentrates stabilized by an organic phosphonic acid compound which sequesters bivalent metal ions. Also, Crommelynck et al, U.S. Pat. No. 4,297,298 discloses the preparation of a stable, dilute solution of peracetic acid using a strong mineral acid catalyst which is stabilized by dipicolinic acid and 2,6-pyridinedicarboxylic acid.

To avoid the hazards of shipping concentrated peroxy acid solutions, higher costs of shipping dilute solutions and problems with storage stability of concentrated solutions, processes for the point-of-use production and dosing of peroxy acids have been proposed. For example, German Patent Application No. DE-36 38 552 teaches generally the point-of-use batch preparation of a peroxy acid by reacting hydrogen peroxide, with a carboxylic acid in the presence of a mineral acid catalyst. These processes have inherent problems associated with the use of a mineral acid catalyst. Strong liquid mineral acids must be handled with the ever-present danger of spills and associated hazards for operators. Additionally, in mineral acid catalyzed point-of-use systems, the product is rather the product stream, therefore, the catalyst is essentially consumed in that it must be continuously replaced. Finally, mineral acid based point-of-use units are generally larger and more costly than resin acid based units requiring the use of more corrosion resistant materials. In contrast, resin acid catalysts may last for several months resulting in a more economical operation.

The use of a cation exchange resin to catalyze the hydrogen peroxide-carboxylic acid reaction has been discussed in the art. U.K. Patent No. 776,758 to duPont discloses the use of cation exchange resins in the preparation of peroxycarboxylic acids from the corresponding carboxylic acid and hydrogen peroxide. This reference apparently did not recognize the problems of resin catalyst swelling. U.S. Pat. No. 4,647,578 to Eckwert et al teaches the epoxidation of hydrocarbons with peroxyacetic acid using a resin catalyst. Included in this disclosure is the generation of peroxyacetic acids in a cation exchange resin. This reference suggests that hydrogen peroxide causes swelling and dissolution of the resin catalyst. Agnihotri et al, "Preparation of Peracetic Acid by Using Various Catalyst Systems", 18 *Colourage* No. 26, page 30 (1971) compares the reaction conversion of mineral acids including sulfuric and phosphoric acids with that using a cation exchange resin at comparable levels of hydrogen ion equivalents. This reference indicates that mineral acids achieve greater conversion than acid resins in the catalysis of the hydrogen peroxide-carboxylic acid reaction.

The prior art taken together suggests that the use of acid resins to catalyze the reaction of hydrogen peroxide and carboxylic acid to produce peroxy acids can cause several problems. First, the hydrogen peroxide can cause swelling and degradation of the acid resin catalyst. Second, the apparent slow rate at which the reaction proceeds using an acid resin can cause a production slowdown or increased costs.

A need exists for a convenient point-of-use process to produce peroxy acid compositions. Preferably, these compositions are free of strong mineral acid catalyst, and the reaction proceeds at rates comparable to or exceeding those obtained using mineral acids. A further need exists for a heterogeneous process of producing peroxy acid compounds which reduces the degradation of catalyst resins.

SUMMARY OF THE INVENTION

We have found that the point-of-use generation of a peroxy acid sanitizing composition can be obtained by reacting an aqueous solution comprising hydrogen peroxide ($H_2O_2$) and a carboxylic acid at a ratio of about 0.1 to 10 moles of $H_2O_2$ per mole of acid in the presence of a strong acid resin catalyst and in the substantial absence of active metal ions. This process forms a mineral acid free aqueous peroxy acid at a concentration up to about 20 wt-% with little catalyst swelling or degradation. Preferably, the resin catalyst swells less than about 25% of the original volume. We have also found that warewashing, laundry, bleach and hard surface sanitizer compositions can be produced using the peroxy acid material generated through the above process.

In one preferred embodiment, the reaction takes place in a column packed with the acid resin allowing for an increased hydrogen ion equivalent concentration. In another preferred embodiment, a swell prevention agent is present in the aqueous reaction solution whereby metal ions are substantially prevented from promoting degradation of the resin.

The term "carboxylic acid" as used in the specification and the claims includes both mono- and dicarboxylic acids.

The phrase "active metal ion" as used in the specification and the claims means metal ions which are capable of promoting resin catalyst degradation.

The phrase "swell prevention agent" as used in the specification and the claims means an agent which is capable of substantially preventing the degradation of the ion exchange resin.

BRIEF DESCRIPTION OF THE DRAWING

FIG. 1 is a schematic diagram of an embodiment of the reaction system of the invention for the production of peroxy acids.

DETAILED DESCRIPTION OF THE PREFERRED EMBODIMENT

Our invention pertains to the reaction of hydrogen peroxide and a carboxylic acid at a ratio of about 0.1 to 10 moles of hydrogen peroxide ($H_2O_2$) per mole of acid in the presence of a strong acid ion exchange resin and in the substantial absence of active metal ions. The resulting peroxy acid solution has a concentration up to about 20 wt-%, and it can then be diluted to the desired concentration upon use. Preferably, the reaction proceeds in the presence of a swell prevention agent.

Our invention also pertains to an apparatus for carrying out the above process. Preferably, the hydrogen peroxide and swell prevention agent are delivered from component supply vessels, 10 and 12 respectively, into a mixing vessel 14. The hydrogen peroxide/swell prevention agent mixture is then pressurized by means of pump 16 and introduced into a packed column 18 through an inlet port 20. At the same time, a carboxylic acid is delivered from a component supply vessel 22, and pressurized by means of pump 24 for delivery through inlet port 20 into packed column 18. The hydrogen peroxide and carboxylic acid are allowed to react as they move up through the packed resin column 18 in the presence of a sulfonic acid resin 28. In order to prevent the upward fluid flow from carrying away the resin 28, the packed column 18 includes a hold down plate 60. Further, for safety reasons, a pressure relief valve 62 is supplied in the column 18. The resulting concentrated aqueous peroxy acid product is preferably discharged through an exit port 30 into a holding tank 32 where it is stored until needed for use. The product exhibits good stability for over a month. At any time, an operator can activate a pump 34 at the discharge of the holding tank 32 to move product to a filling station 36. At the filling station 36 the operator can also activate a water supply pump 38 to move water from a water supply 40 thereby diluting the peroxy acid compound to a use concentration.

In a more preferred embodiment, upper and lower sensors 42 and 44 respectively are located in the holding tank 32 to sense when the tank is both nearly full and nearly empty. Sensing signals 46 are sent from sensing means 42 and 44 to a processing means 48 where the information is processed. The processing means produces a controlling signal 50 which is relayed to controlling means 52. This controlling means controls pumps 16, 24, 56 and 58 which in turn control the input of reactants from the supply vessels 14, 22, 10 and 12 respectively.

Reactants

The hydrogen peroxide used in the present invention is available from many commercial sources. Preferably, it is used as an aqueous solution at about 10 to 75 wt-% hydrogen peroxide. More preferably, for safety, ease of handling and completion of reaction, the hydrogen peroxide reactant is present at about 25 to 50 wt-% hydrogen peroxide.

The carboxylic acid used in the present invention may be any carboxylic acid which can react with hydrogen peroxide to form a peroxycarboxylic acid. Such acids include formic, propionic and acetic acid, as well as glycolic, lactic, tartaric and malic acids. Dicarboxylic acids such as succinic and adipic acids may also be used. Preferably, the carboxylic acid is a food grade acid. This allows the resulting peroxy acid to degrade into chemicals which are fit for human consumption. A particularly preferred carboxylic acid for use in the present invention is acetic acid.

The carboxylic acid is preferably introduced as an aqueous solution of from about 10 to 100 wt-% carboxylic acid. More preferably, for completion of reaction, it is introduced as about 40 to 100 wt-% carboxylic acid.

Catalyst

The catalyst used in the present invention is a strong acid ion exchange resin catalyst. These resins generally comprise a styrene-divinyl benzene copolymer backbone and ionic functional groups. The relative portion of divinyl benzene in the copolymer resin backbone is generally measured in percentages and is also termed the degree of crosslinking. The degree of crosslinking is preferably from about 1% to about 50%; more preferably, it is from about 8% to about 20%. Most preferably, the ion exchange resin is from about 10%-20% crosslinked.

The ion exchange resin may be a gel type resin or a macroreticular resin. Gelular resins are rigid, transparent spherical beads with a homogeneous polymeric matrix. Macroreticular resins consist of agglomerates of very small gelular microspheres fused together into a much larger macrosphere closer in size to the usual gel bead. Based on preliminary data, it appears that gelular resins may have improved resistance to swelling in comparison to macroreticular resins.

Due to the heterogeneous nature of the acid resin catalyst/liquid reagent system, the sulfonic acid resin acts as a true catalyst. Unlike the case with aqueous mineral acid catalysts, there is no need to continually replenish the acid resin catalyst in the present invention. There is also no need to regenerate the column.

Strong acid ion exchange resins are generally prepared using sulfonated styrene monomers or by the sulfonation of the styrene-divinyl benzene copolymer and have the partial structure, $RSO_3H$, wherein R represents the resin. The strong acid resins generally remain highly ionized in both their acid and salt forms. Additionally, strong acid resins behave in a manner similar to strong mineral acids.

Strong acid ion exchange resins are available in both the acid form and its corresponding salt form. Preferably, the resin is used in an acid form. Strong acid ion exchange resins are available from the Dow Chemical Company under the DOWEX TM mark and from Rohm & Haas under the AMBERLYST TM mark.

Swell Prevention Agent

As indicated above, a swell prevention agent substantially prevents the degradation of the strong acid resin catalyst. Such an agent may operate through various mechanisms including precipitation and chelation. A precipitation/filtration process could essentially remove the offending active metal ions from the reaction stream prior to contact with the resin catalyst. However, the swell prevention agent is preferably a chelating agent.

A chelating agent is an organic or inorganic molecule or ion that coordinates a metal ion, typically a di-or trivalent metal ion, in more than one position, i.e., two or more electron donor groups in the molecule. However, preferred chelators are primarily organic compounds which are classified by the number of coordinating groups present, i.e., bidentate, terdentate or tridentate, quadridentate or tetradentate, etc. Common chelating agents include those compounds which have oxygen or nitrogen donor atoms, as well as, in some cases, thiol or mercapto compounds. Representative, non-limiting organic chelating agents which are useful in the present invention are those which are compatible in a strong oxidizing medium and include amino carboxylic acids such as ethylenediaminetetraacetic acid (EDTA), hydroxyethylenediaminetriacetic acid (HEDTA), nitrilotriacetic acid (NTA), diethylenetriaminepentaacetic acid (DTPA), n-hydroxyethyleneaminodiacetic acid; organic polyphosphates such as phytic acid; polymeric carboxylates such as polyacrylic acid, polymethacrylic acid, polyitaconic acid, polymaleic acid, and copolymers thereof; alphahydroxy acids such as citric, tartaric, ascorbic, and isoascorbic; quinolines such as 8-hydroxyquinoline and 5-sulfo-8-hydroxyquinoline; carboxy pyridines such as 2,6-pyridinedicarboxylic acid; and organic phosphonates such as 1-hydroxyethylidene-1,1-diphosphonic acid, aminotri(methylene phosphonic acid), ethylenediaminetetra(methylene phosphonic acid), diethylenetriaminepenta(methylene phosphonic acid), ethanolamine-n,n-di-(methylene phosphonic acid) and 2-phosphonobutane-1,2,4-tricarboxylic acid. Representative, non-limiting inorganic chelating agents include condensed phosphates such as tripolyphosphate, polyphosphates, polyphosphonates, pyrophosphates, and metaphosphates.

The chelating agent of our invention is preferably an organic polyphosphonate, and more preferably it is a di-or triphosphonate. These phosphonates are available from Monsanto Chemical Company under the trademark DEQUEST ®. Most preferably it is 1-hydroxyethylidene-1,1-diphosphonic acid or its salt (DEQUEST® 2010, available from Monsanto Chemical Co.). The chelating agent is present preferably from about 0.1 to 15 wt-% of the reactants. More preferably it is present at about 0.5 to 10 wt-%. The use of the chelating agent increases the life of the resin catalysts, and it significantly reduces the catalyst swelling.

Other Purification Methods

Other methods may be used to provide for the substantial absence of active metal ions during the reaction. Two such methods include (1) the purchase and use of pure reagent sources and inert process equipment and (2) the use of a cation exchange resin to purify the reagents prior to their introduction into the acid resin catalyst portion of the reactor. In any of these processes, the strong acid resin catalyst may also be pretreated with multiple washes of an aqueous chelating agent or strong mineral acid to remove metal impurities which may be present.

In any event, the active metal ions must be reduced to a level sufficiently low enough to prevent the active metal ion from promoting the degradation of the strong acid resin catalyst.

While we do not wish to be held to this theory, we believe that the reduction of swelling of the strong acid resin catalyst is due to the elimination, or at least significant reduction in concentration, of active metal ions in the reaction stream. We believe that these active metal ions would otherwise be available to promote the degradation of the resin catalyst.

Reaction Condition

The hydrogen peroxide-carboxylic acid reaction runs at a temperature from less than 50° C. preferably. At temperatures greater than about 50° C., the resin catalyst life is decreased and the resin ultimately forms a gel.

Additionally, at lower temperatures, degradation of the ion exchange resin is reduced. With reaction temperatures at ambient (about 25° C.) or below, the amount of swelling can be decreased by a factor of about 7 compared with the resin swelling life at 50° C.

The reaction time is controlled by the residence time of the material in the reactor, and it is preferably up to about 60 minutes. More preferably, the residence time is from about 2 to 45 minutes. Preferably, the reaction is a continuous reaction and proceeds at ambient pressure.

The peroxy acid of our invention is preferably produced in a concentrated form at about 2% to 20% of the aqueous product. More preferably, it is present at about 10% to 20%, and most preferably, at about 14% to 19%. The peroxy acid product may then be diluted to use concentrations.

While the reaction may take place in any reaction system, the preferred reactor is a packed column reactor. As used in the specification and the claims, the phrase "packed column" means any reactor vessel or configuration in which the reactants flow through the resin which is essentially prevented from travelling with the reaction stream. A representative, non-limiting list of such reactors includes a packed tower and a resin bed. Preferably, the column is packed with the acid resin catalyst such that the resin occupies the majority of the reactor. In this manner, void space is formed between the resin beads. It is through these voids and by diffusion into the resin beads that the aqueous reactants flow. This arrangement allows the hydrogen peroxide-carboxylic acid reaction to occur under continuously flowing conditions; the reactants are introduced under pressure into the bottom region of the packed column and flow upwards through the resin. The product is then removed from the top of the packed column.

Uses of Peroxy Acid

The peroxy acid of our invention can be used for sanitizing and/or bleaching in various industrial settings. Representative, non-limiting users of our process include dairies, breweries, laundries, water treatment plants, warewashing processes, pulp and paper manufacturers, bottling plants and pharmaceutical and medical facilities.

In using the peroxy acid, it is generally diluted with water to a use concentration. The dilute peroxy acid is then applied to the objects or surfaces to be sanitized and/or bleached. Depending on the peroxy acid used, the presence of small amounts of the product remaining on the surfaces or objects can be safe as peroxy acids produced from food grade carboxylic acids decompose into water and the parent carboxylic acid which is safe for human consumption at low concentrations.

The preferred uses of the peroxy acid produced in our process and useful concentration ranges for these products are shown in Table I. The preferred use concentration is very dependent on the use temperature. At higher use temperature, e.g., 50–80° C., better bleaching and faster bactericide kill is normally obtained.

TABLE I

| End Use | Useful Peroxy Acid Concentration Range (ppm) | Preferred Peroxy Acid Concentration Range (ppm) |
| --- | --- | --- |
| Warewashing Laundry | about 5–200 | about 10–50 |
| Sanitizer | about 5–500 | about 25–300 |
| Bleach | about 5–500 | about 50–300 |
| Hard Surface Sanitizer | about 5–500 | about 50–300 |

Additionally, surfactants may also be incorporated into the warewashing or bleaching solution.

EXAMPLES

Example 1

A stock peroxyacetic acid solution was prepared by mixing equal weights of hydrogen peroxide (35% hydrogen peroxide and water) and glacial acetic acid and allowing the mixture to stand for several days until an equilibrium mixture was obtained. A sample of the stock solution was titrated and the percent peroxyacetic acid was determined to be 16.8%. Solutions for each inhibitor and concentration to be tested were prepared from the stock solution. A strong sulfonic acid resin was soaked in distilled water for three days. The resin was added to a 10 milliliter graduated cylinder until the level reached 4 milliliters. Excess water was pipetted off. The resin was washed twice with the appropriate peroxyacetic acid solution. Sample solutions (of peroxyacetic acid and inhibitors) were added to bring the volume to 7 milliliters. The sample was corked and shaken gently. The cylinders were placed in water bath at 120° F. The height of the resin was checked at various periods and the sample liquid was replaced with fresh samples from stock solutions. Because of the size limitations of the cylinders, the maximum height recorded was 10 milliliters. The results are shown below in Table II.

TABLE II

Effect of Inhibitors on Resin Swelling Resistance
Resin Height, mls

| # | % Inhibitor | Description | Days In Test | | | | | |
|---|---|---|---|---|---|---|---|---|
| | | | 6 | 15 | 22 | 26 | 30 | 33 |
| 1 | 0.5% | Aminotri | 4.2 | 5.1 | 5.4 | 5.6 | 5.8 | 6.2 |
| 2 | 1.0% | (methylene | 4.2 | 4.6 | 4.9 | 5.0 | 5.2 | 5.2 |
| 3 | 1.5% | phosphonic | 4.2 | 4.6 | 4.6 | 4.6 | 4.8 | 4.8 |
| 4 | 2.0% | acid)[1] | 4.2 | 4.4 | 4.5 | 4.4 | 4.6 | 4.6 |
| 5 | 0.5% | 1-hydroxy- | 4.3 | 5.0 | 5.4 | 5.6 | 6.0 | 6.5 |
| 6 | 1.0% | ethylidene- | 4.2 | 4.8 | 5.2 | 5.6 | 5.8 | 6.4 |
| 7 | 1.5% | 1,1-diphos- | 4.3 | 4.8 | 5.2 | 5.6 | 5.8 | 6.4 |
| 8 | 2.0% | phonic acid[2] | 4.3 | 4.9 | 5.2 | 5.5 | 5.8 | 6.3 |
| 9 | 0.5% | Diethylenetriamine | 4.0 | 4.2 | 4.2 | 4.2 | 4.2 | 4.2 |
| 10 | 1.0% | penta(methylene | 4.0 | 4.0 | 4.0 | 4.0 | 4.0 | 4.0 |
| 11 | 1.5% | phosphonic acid)[3] | 4.0 | 4.0 | 4.0 | 4.0 | 4.0 | 4.0 |
| 12 | 2.0% | | 4.0 | 4.0 | 4.0 | 4.0 | 4.0 | 4.0 |
| 13 | 0.5% | EDTA-Na4 | 4.4 | 5.4 | 6.6 | 4.6 | 9.6 | 10+ |
| 14 | 1.0% | | 4.4 | 5.4 | 6.3 | 7.2 | 8.8 | 10+ |
| 15 | 1.5% | | 4.3 | 5.2 | 6.0 | 6.7 | 7.6 | 8.5 |
| 16 | 2.0% | | 4.2 | 5.0 | 5.8 | 6.2 | 6.3[5] | 6.5 |
| 17 | 0.5% | NTA Na3—H2O | 4.4 | 5.2 | 6.4 | 7.3 | 9.0 | 10— |
| 18 | 1.0% | | 4.3 | 5.2 | 6.1 | 7.0 | 7.8 | 10— |
| 19 | 1.5% | | 4.3 | 5.2 | 6.1 | 7.0 | 8.2 | 9.2 |
| 20 | 2.0% | | 4.2 | 5.0 | 6.1 | 6.3 | 6.4 | 6.8 |
| 21 | 0.5% | Citric acid | 4.4 | 5.6 | 6.8 | 8.0 | 9.8 | 10+ |
| 22 | 1.0% | | 4.4 | 5.4 | 6.6 | 7.6 | 9.6 | 10+ |
| 23 | 1.5% | | 4.4 | 5.4 | 6.6 | 7.6 | 9.2 | 10+ |
| 24 | 2.0% | | 4.4 | 5.5 | 6.6 | 7.6 | 9.3 | 10+ |
| 25 | 0.5% | 2-phosphonobutane- | 4.4 | 5.4 | 6.6 | 7.4 | 9.0 | 10+ |
| 26 | 1.0% | 1,2,4-tricarbox- | 4.4 | 5.4 | 6.5 | 7.4 | 8.7 | 10+ |
| 27 | 1.5% | ylic acid[4] | 4.4 | 5.4 | 6.5 | 7.2 | 8.6 | 10+ |
| 28 | 2.0% | | 4.4 | 5.4 | 6.4 | 7.2 | 8.4 | 10+ |
| 29 | 0.5% | 2,6-pyridine | 4.4 | 5.6 | 6.8 | 7.9 | 9.6 | 10+ |
| 30 | 1.0% | dicarboxylic | 4.5 | 5.6 | 6.8 | 7.7 | 8.9 | 10+ |
| 31 | 1.5% | acid | — | — | — | — | — | — |
| 32 | 2.0% | | — | — | — | — | — | — |
| 33 | — | None | 4.4 | 5.4 | 6.6 | 7.6 | 9.3 | 10+ |

[1]DEQUEST ® 2000, available from Monsanto Company
[2]DEQUEST ® 2010, available from Monsanto Company
[3]DEQUEST ® 2060, available from Monsanto Company
[4]BAYHIBIT AM, available from Mobay Chemical Corp.
[5]Some of the resin became stuck on the cork and was discarded From the above data it appears that the phosphonate compounds were the most effective agents in reducing the swelling of the acid resin at all concentration levels.

Example 2

Samples were taken from stock solutions of Example 1 after seven (7) weeks and titrated to determine the percent peroxyacetic acid. The results are shown below in Table III.

TABLE III

Stability of Peroxyacetic Acid in Presence of Inhibitor

| Sample # | % Inhibitor | Description | % Peroxyacetic Acid |
|---|---|---|---|
| 1 | 0.5% | Aminotri (methylene | 8.72 |
| 2 | 1.0% | phosphonic acid)[1] | 4.54 |
| 3 | 1.5% | | 2.45 |
| 4 | 2.0% | | 1.36 |
| 5 | 0.5% | 1-hydroxyethylidene- | 16.88 |
| 6 | 1.0% | 1,1-diphosphonic | 15.75 |
| 7 | 1.5% | acid[2] | 15.50 |
| 8 | 2.0% | | 13.03 |
| 9 | 0.5% | Diethylenetriamine | 0.29 |
| 10 | 1.0% | penta(methylene | 0.33 |
| 11 | 1.5% | phosphonic acid) | 0.24 |
| 12 | 2.0% | | 0.22 |
| 13 | 0.5% | EDTA-Na4 | 13.82 |
| 14 | 1.0% | | 11.27 |
| 15 | 1.5% | | 7.03 |
| 16 | 2.0% | | 4.54 |
| 17 | 0.5% | NTA Na3—H2O | 13.48 |
| 18 | 1.0% | | 12.60 |
| 19 | 1.5% | | 9.48 |
| 20 | 2.0% | | 9.19 |
| 21 | 0.5% | Citric Acid | 15.96 |
| 22 | 1.0% | | 16.01 |
| 23 | 1.5% | | 16.08 |
| 24 | 2.0% | | 15.97 |
| 25 | 0.5% | 2-phosphonobutane-1,2,4- | 16.06 |
| 26 | 1.0% | tricarboxylic acid[4] | 15.62 |
| 27 | 1.5% | | 15.16 |
| 28 | 2.0% | | 14.73 |
| 29 | 0.5% | 2,6-pyridine | 16.62 |
| 30 | 1.0% | dicarboxylic | 17.23 |
| 31 | 1.5% | acid | — |
| 32 | 2.0% | | — |
| 33 | | None | 17.48 |

[1]DEQUEST ® 2000, available from Monsanto Company
[2]DEQUEST ® 2010, available from Monsanto Company
[3]DEQUEST ® 2060, available from Monsanto Company
[4]BAYHIBIT AM ™, available from Mobay Chemical Corp.

These data indicate that peroxyacetic acid is not le with all phosphonates. Therefore, a preferred chelating agent would combine swelling reduction and peroxyacetic acid stability, e.g., 1-hydroxyethylidene-1,1-diphosphonic acid.

Example 3

A series of reactions were performed using a 1.5:1 mole ratio of acetic acid to hydrogen peroxide to compare the use of homogeneous sulfuric acid catalysts with a heterogeneous sulfonic acid resin catalyst. The reactions took place at 75° F., the reaction time is indicated below in Table IV (actual time for batch reaction or residence time for continuous flow reaction) as is the reaction type and the proportion of the homogeneous sulfuric acid catalyst. The sulfonic acid resin catalyst was present in a packed column reactor. The resulting concentration of the product peroxyacetic acid for each reaction type is shown below in Table IV.

TABLE IV

Reaction Rate Comparison

| Catalyst | H+Eq/l | Reaction-type | % Peroxyacetic Acid 30 min | % Peroxyacetic Acid 60. min |
|---|---|---|---|---|
| 5% H$_2$SO$_4$ | 1.1 | Continuous | 7.9 | 8.4 |
| 10% H$_2$SO$_4$ | 2.2 | Continuous | 14.0 | N/A |
| 5% H$_2$SO$_4$ | 1.1 | Batch | 11.0 | 12.6 |
| Sulfonic Acid Resin* | 7.2 | Continuous | 15.1 | 16.5 |

*AMBERLYST ™ 15 is available from Rohm & Haas Co.

The data illustrates that the use of a packed column of sulfonic acid catalyst resin allows a higher concentration of acid (equivalents of H+ per liter of liquid) than a 10% mineral acid catalysts and, therefore, a faster conversion rate to peroxyacetic acid.

Example 4

A 20% crosslinked macroreticular sulfonic acid resin was placed in each of two 8 oz. glass jars containing approximately 14% to 16% peroxyacetic acid, 8% to 10% hydrogen peroxide, 30% acetic acid and the balance water. The concentration of peroxyacetic acid and hydrogen peroxide were checked every week, and additional hydrogen peroxide and acetic acid were added as necessary to maintain the peroxyacetic acid content between 14% and 16% and the hydrogen peroxide content between 8 and 10%. The solutions were maintained at ambient temperature (about 75° F.). A second solution was prepared as above, and to it was added about 1% of a solution of 1-hydroxyethylidene-1,1-diphosphonic acid. The volume percent swelling of the resin was calculated by measuring the increase in height of the resin over time. The results are indicated below in Table V.

TABLE V

The Effect of a Chelating Agent on the Stability of a Sulfonic Acid Resin at Ambient Temperature (Volume Percent Swelling)

| Sample | Month 1 | 2 | 3 | 4 | 5 | 6 |
|---|---|---|---|---|---|---|
| Control | 7.1 | 14.3 | 15.2 | 18.8 | 23.3 | 28.2 |
| W/Chelating Agent | 0.0 | 2.2 | 4.2 | 8.0 | 8.0 | 14.8 |

These data indicate that the use of a chelating agent at ambient temperature greatly reduces the amount of swelling of the sulfonic acid resin. Additionally, comparing the data from Table V with that shown in Table II indicates that operating the system at lower temperatures greatly reduces the amount of swelling of the sulfonic acid resin catalyst.

Efficacy of Peroxyacetic Acid on Sanitizing

Various concentrations of the peroxyacetic acid of our invention were applied to cultures of *S. aureus* for 30 seconds at several temperatures. The average log reduction of *S. aureus* population in the culture (as a measure of sanitizer efficacy) is illustrated below in Table VI.

TABLE VI

Peroxyacetic Acid Against *S. aureus* at 30 Second Exposures in Distilled Water

| pH | Temp. | Conc. POAA | Ave. Log Reduction Trial 1 | Trial 2 |
|---|---|---|---|---|
| 6.0 | Room | 120 ppm | 4.70 | 5.7 |

TABLE VI-continued

Peroxyacetic Acid Against *S. aureus* at 30 Second Exposures in Distilled Water

| pH | Temp. | Conc. POAA | Ave. Log Reduction Trial 1 | Trial 2 |
|---|---|---|---|---|
| | 120° F. | 100 ppm | >7.15 | >7.15 |
| | 120° F. | 50 ppm | >7.15 | >7.15 |
| 6.5 | Room | 120 ppm | 5.08 | 6.30 |
| | 120° F. | 100 ppm | >7.15 | >7.15 |
| | 120° F. | 50 ppm | >7.15 | >7.15 |
| 7.0 | Room | 120 ppm | 5.80 | 4.70 |
| | 140° F. | 100 ppm | >7.15 | >7.15 |
| | 140° F. | 50 ppm | >7.15 | >7.15 |
| 7.5 | Room | 120 ppm | 4.79 | 4.62 |
| | 140° F. | 100 ppm | >7.15 | >7.15 |
| | 140° F. | 50 ppm | >7.15 | >7.15 |

The above specification, examples and data demonstrate that the use of a chelating agent in conjunction with the hydrogen-peroxide and carboxylic acid reactants protect the strong acid ion exchange resin catalyst bed from swelling and decomposition during reaction and produce a relatively stable peroxy acid composition. Further the data shows a significant increase in productivity of peroxyacetic acid due to the greater acid equivalent concentration using a continuous resin catalyzed reaction system.

The product of the process of the invention results in significant and sanitizing kills of micro-organisms at typical use concentrations of temperatures for the peroxy acid material.

While the above discussion, examples, tables and data disclose and demonstrate the invention as it is currently understood by the inventors, the invention can take a variety of embodiments without departing from the scope and spirit of the invention. The invention is embodied in the claims herein and after appended.

We claim:

1. A process for the point-of-use generation of a peroxyacetic acid containing composition, which process comprises:
    (a) introducing hydrogen peroxide and acetic acid into a packed column at a ratio of about 0.1 to 10 moles of hydrogen peroxide per mole of acetic acid; and
    (b) reacting the hydrogen peroxide and acetic acid in an aqueous solution comprising about 0.1 to 15 wt-% swell prevention agent in the presence of a strong acid resin catalyst at a reaction temperature of less than about 50° C. to form an aqueous peroxyacetic acid composition at a concentration from about 10 to 20 wt-%.

2. The process of claim 1 which comprises about 0.25 to 4 moles of the hydrogen peroxide per mole of acetic acid.

3. The process of claim 1 wherein the swell prevention agent comprises a chelating agent.

4. The process of claim 3 wherein the chelating agent comprises an organic chelating agent.

5. The process of claim 4 wherein the organic chelating agent comprises a polyphosphonate.

6. The process of claim 5 wherein the polyphosphonate comprises a di- or triphosphonate or mixtures thereof.

7. The process of claim 6 wherein the chelating agent comprises 1-hydroxyethylidene-1,1-diphosphonic acid.

8. The process of claim 3 wherein the chelating agent is present at about 0.1 to 2.0 wt-%.

9. The process of claim 1 wherein the strong acid resin comprises a sulfonic acid resin.

10. The process of claim 1 wherein the strong acid resin has a degree of crosslinking of about 8% to about 20%.

11. The process of claim 1 wherein the resin swells to less than about 25% of the original resin volume.

12. The process of claim 1 further comprising maintaining the reactants in contact with the catalyst for about 15 to 45 minutes.

13. A process for the point-of-use generation of a peroxy-carboxylic acid sanitizing and bleaching composition, which process comprises:
   (a) introducing aqueous hydrogen peroxide and a carboxylic acid at a ratio of about 0.1 to 10 moles hydrogen peroxide per mole of carboxylic acid and a swell prevention agent into a reactor containing a strong acid resin catalyst; and
   (b) passing the aqueous solution of hydrogen peroxide, carboxylic acid and swell prevention agent through the strong acid resin catalyst at a reaction temperature of less than about 50° C. to form an aqueous peroxycarboxylic acid composition at a concentration up to about 20 wt-% peroxycarboxylic acid.

14. The process of claim 13 wherein the hydrogen peroxide, carboxylic acid and swell prevention agent are passed generally upward through the acid resin catalyst.

15. The process of claim 13 wherein the peroxy carboxylic acid is essentially free of strong mineral acids which may promote corrosion of equipment.

16. The process of claim 13 wherein the reaction proceeds in the substantial absence of active metal ions available to promote degradation of the resin catalyst.

17. The process of claim 13 wherein metal ions are substantially precipitated and removed from the aqueous solution prior to contact between the solution and the catalyst.

18. The process of claim 13 wherein the swell prevention agent is present at about 0.1 to 15 wt-% of the aqueous solution.

19. The process of claim 13 wherein the swell prevention agent comprises a chelating agent.

20. The process of claim 13 wherein the ratio comprises about 0.25 to 4 moles of hydrogen peroxide per mole of carboxylic acid.

21. The process of claim 13 wherein the reactor comprises a packed column.

22. The process of claim 19 wherein the chelating agent comprises an organic chelating agent.

23. The process of claim 22 wherein the organic chelating agent comprises a polyphosphonate.

24. The process of claim 23 wherein the polyphosphonate comprises a di- or triphosphonate or mixtures thereof.

25. The process of claim 24 wherein the chelating agent comprises 1-hydroxyethylidene-1,1-diphosphonic acid.

26. The process of claim 19 wherein the chelating agent is present at about 0.1 to 2.0 wt-%.

27. The process of claim 13 wherein the strong acid resin comprises a sulfonic acid resin.

28. The process of claim 13 wherein the strong acid resin catalyst has a degree of cross-linking from about 1% to 50%.

29. The process of claim 28 wherein the strong acid resin catalyst has a degree of crosslinking from about 8% to 20%.

30. The process of claim 13 wherein the resin swells to less than about 25% of the original resin volume.

* * * * *